United States Patent [19]

Kopolow et al.

[11] Patent Number: 5,169,623
[45] Date of Patent: * Dec. 8, 1992

[54] CONDITIONING HAIR CARE COMPOSITIONS

[75] Inventors: Stephen L. Kopolow, Plainsboro; William J. Burlant, Wayne; Michael W. Helioff, Westfield; Carmen D. Bires, Hackettstown; Robert B. Login, Oakland; Mohammed Tazi, Wayne, all of N.J.

[73] Assignee: ISP Investments Inc., Wilmington, Del.

[*] Notice: The portion of the term of this patent subsequent to Dec. 17, 2008 has been disclaimed.

[21] Appl. No.: 638,598

[22] Filed: Jan. 8, 1991

Related U.S. Application Data

[63] Continuation-in-part of Ser. No. 510,017, Apr. 17, 1990, abandoned, and a continuation-in-part of Ser. No. 604,263, Oct. 29, 1990, Pat. No. 5,073,296.

[51] Int. Cl.⁵ .......................... A61K 7/15; B01J 13/00
[52] U.S. Cl. .................................. 424/47; 252/312; 252/89.1; 424/59; 424/70; 424/71; 424/73; 514/557; 514/772.7; 514/847
[58] Field of Search ................. 252/312, 89.1; 424/73, 424/59, 45, 70, 71; 514/557, 772

[56] References Cited

U.S. PATENT DOCUMENTS

| | | | |
|---|---|---|---|
| 4,923,695 | 5/1990 | Nowak, Jr. et al. | 424/71 |
| 4,933,170 | 6/1990 | Nowak, Jr. et al. | 424/67 |
| 4,940,576 | 7/1990 | Walsh | 424/70 |
| 5,034,220 | 7/1991 | Helioff et al. | 424/73 |

Primary Examiner—Richard D. Lovering
Assistant Examiner—N. Bhat
Attorney, Agent, or Firm—Walter Katz; Marilyn J. Maue; Joshua J. Ward

[57] ABSTRACT

What is provided herein are conditioning hair care compositions comprising (a) a stabilized silicone product obtained by in situ polymerization of a water-soluble vinyl monomer, preferably vinylpyrrolidone, in the presence of discrete microdroplets of a silicone oil in water, (b) a surfactant, and the balance being (c) water.

28 Claims, No Drawings

CONDITIONING HAIR CARE COMPOSITIONS

CROSS-REFERENCE TO RELATED PATENT APPLICATIONS

This application is a continuation-in-part of copending U.S. patent applications Ser. No. 510,017, filed Apr. 17, 1990 now abandoned and Ser. No. 604,263, filed Oct. 29, 1990, U.S. Pat. No. 5,073,296 respectively, and assigned to the same assignee as herein.

BACKGROUND OF THE INVENTION

1. Field of the Invention

This invention relates to conditioning hair care compositions, and more particularly, to silicone-containing hair care formulations.

2. Description of the Prior Art

Conditioning hair care compositions in the form of shampoos, mousses and conditioners are commercial formulations for personal hair care use. A conditioning shampoo, for example, contains both a surfactant component for effective shampoo action, and a lubricant or resin material which conditions the hair. The use of silicones in conditioning shampoos is well known in the art. See, for example, U.S. Pat. Nos. 3,957,970; 4,472,375; 4,559,227; 4,586,518; 4,728,457; 4,741,855; 4,749,565; 4,749,732; 4,788,006; and 4,849,127. However, these and other patents and publications have not been entirely satisfactory in providing stable dispersions of silicones in an aqueous formulation, and/or an effective hair conditioning shampoo product.

Accordingly, it is an object of the invention to provide a conditioning hair care composition in the form of shampoo, mousse or conditioner which contains silicone in stable, dispersed form.

Another object of this invention is to provide a silicone-containing shampoo which has advantageous properties for the user.

Still another object is to provide a homogeneous silicone-containing shampoo which can be formulated by a simple process.

These and other objects and features of the invention will be made apparent by the following description of the invention herein.

Unless otherwise indicated, all percentages and ratios herein are by weight.

SUMMARY OF THE INVENTION

What is provided herein is a conditioning hair care composition comprising (a) a stabilized silicone product obtained by in situ polymerization of a water-soluble vinyl monomer, preferably vinylpyrrolidone, in the presence of discrete microdroplets of a silicone oil in water, (b) a surfactant, and the balance being (c) water.

DETAILED DESCRIPTION OF THE INVENTION

The essential as well as optional components are described below.

Stabilized Silicone Product

The active material to be dispersed in an aqueous medium are silicone oils which are water-insoluble liquids at room temperature, and are cosmetically-active, i.e. they impart hair conditioning and style retention properties to hair care formulations.

Suitable silicone oils or fluids for use in the invention are selected from non-volatile polyalkyl siloxanes, polyaryl siloxanes, polyalkylaryl siloxanes and polyether siloxane copolymers. Mixtures of these compounds also may be used as long as the final mixture is non-volatile and the dispersed silicone particles are insoluble in the aqueous medium. As used herein, "insoluble" requires that the oil does not substantially dissolve in water and is essentially immiscible therewith.

Non-volatile polyalkylsiloxanes include, for example, polydimethylsiloxanes (Dimethicone) with viscosities ranging from about 5–600,000 centistokes (cs) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul. 20, 1970. Preferably, the viscosity of these siloxanes selected have a viscosity of about 100 to about 100,000 cs, and most preferably, a viscosity of up to about 15,000 cs.

Suitable non-volatile polyalkylarylsiloxanes include, for example, polymethylphenylsiloxanes having viscosities of about 15 to 65 cs at 25° C. These siloxanes are available, for example, from the General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to 100,000 cs at 25° C. are useful.

These and other suitable silicones are disclosed in U.S. Pat. Nos. 2,826,551, 3,964,500 and 4,364,837; and British Patent 849,433. The disclosures of these patents are incorporated by reference herein, as is the booklet "Silicone Compounds", which was distributed by Petrarch Systems Inc. in 1984, and which describes the preparation and properties of available silicones for use in this invention.

In the practice of the present invention, the silicone oil to be dispersed is first added to water and then subjected to agitation to produce a fine dispersion of discrete silicone oil microdroplets throughout the aqueous medium. The mixture is agitated sufficiently so that the dispersion is stable for a period of at least 5 to 10 minutes without separating into individual layers. Conventional laboratory and high speed agitators may be used for this purpose, as for example, conventional anchor or wide-span turbine agitators.

Thereafter, a water-soluble vinyl monomer, for example, a vinylpyrrolidone monomer such as vinylpyrrolidone itself or a derivative thereof such as an alkyl vinyl pyrrolidone, is added to the mixture, along with an appropriate free radical polymerization initiator.

Suitable free radical polymerization initiators for polymerization of water-soluble vinyl monomers include such free radical catalysts as t-butylperoctoate, t-butylperoxy- pivalate and the like. Oil-soluble catalysts are preferred.

Thereafter, the reaction mixture is maintained at a temperature in the range of about 55° to 85° C., preferably, about 75° to 85° C., and most preferably, about 78° to 82° C., for a period of time sufficient to effect the desired polymerization and form the aqueous polymer solution necessary to stabilize the discrete microdroplets of the silicone oil.

As the polymerization proceeds, the dispersed silicone microdroplets become white and appear to precipitate in the aqueous medium, however, without coalescing. Generally, the observance of this white or milky color in the aqueous medium is an indication of completion of the process, which usually takes about 2 to 20 hours, preferably about 4 to 10 hours, and most preferably, about 6 to 8 hours. After completion of polymerization, the residual vinyl monomer content generally is less than about 0.1%, as measured by the iodine titration method.

The production of stable, discrete microdroplets of silicone oil in the resulting aqueous polymer solution can be controlled by the viscosity of the aqueous polymer solution. For example, the viscosity of this medium can be increased by increasing the relative amount of vinyl monomer to oil in the original reaction mixture. By increasing the viscosity of the polymer solution, the proclivity to form a stable, homogeneous suspension of discrete microdroplets of oil throughout the entire medium is enhanced. On the other hand, reducing the viscosity of the medium by decreasing the amount of vinyl monomer in the initial mixture results in a more dilute concentration of polyvinyl polymer in the resultant mixture, which enhances the tendency to form a separate layer of discrete oil droplets.

Suitably, the ratio of vinyl monomer to silicone oil used in the polymerization should be in the range of about 95/5 to 5/95, respectively, on a weight basis, preferably at least about 50/50. Most preferred is a range of about 90/10 to 70/30. As used herein, a "stable composition or suspension" means that the discrete oil microdroplets remain suspended in the aqueous polymer solution for at least seven days at ambient temperature.

The viscosity of the stabilized silicone oil in water product, which is obtained by in situ polymerization of vinylpyrrolidone monomer, suitably is in the range of about 3,000 to 100,000 cps, preferably about 4,000 to 60,000 cps, and most preferably, about 6,000 to 25,000 cps.

The diameter of the silicone microdroplets obtained are observed to be in the range of about 0.1 to 450 microns, and usually are about 1 to 100 microns.

Surfactants

The surfactants useful in the conditioning hair care compositions of this invention can be present at a level of from about 1% to about 30%, most preferably from about 5% to about 25% of the composition. Surfactants useful in compositions of the invention include anionic, nonionic, cationic, zwitterionic and amphoteric surfactants.

Synthetic anionic detergents useful herein, particularly for the shampoo compositions, include alkyl and alkyl ether sulfates. These materials have the respective formulae $ROSO_3M$ and $RO(C_2H_4O)_xSO_3M$ where R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 12 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sldium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oide. Such a mixture also comprises from about 0 to 20% by weight $C_{12-13}$ compounds; from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8:, and from about 0.1 to 15% by weight of compounds having a degree of ethoxylation greater than 8.

Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e g., $SO_3$, $H_2SO_4$ oleum, obtained according to known sulfonation methods, including bleaching and hydrolysis. Preferred are alkali metal and ammonium sulfonated $C_{12-18}$ n-paraffins.

Additional examples of anionic synthetic detergents which come within the terms of the present invention are the reaction products of fatty acids esterified with isethionic acid and neutralized with sodium hydroxide where, for example, the fatty acids are derived from coconut oil; sodium or potassium salts of fatty acid amines of methyl tauride in which the fatty acids, or example, are derived from coconut oil. Other anionic synthetic detergents of this variety are set forth in U.S. Pat. Nos. 2,486,921; 2,486,922; and 2,396,278.

Still other anionic synthetic detergents include the class designated as succinamates. This class includes such surface active agents as disodium N-octadecylsulfosuccinamate, tetrasodium N-(1,2-dicarboxyethyl)-N-octadecylsulfo-succinamate, diamyl ester of sodium sulfosuccinic acid; dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid SO₂, chlorinated hydrocarbons, etc., when used in the liquid form, or by air, nitrogen, gaseous SO₂, etc., when used in the gaseous form.

The alpha-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880 of Phillip F. Pflaumer and Adrian Kessler, issued Jul. 25, 1967, titled "Detergent Composition", the disclosure of which is incorporated herein by reference.

Another class of anionic organic detergents are the beta-alkyloxy alkane sulfonates. There compounds have the following formula:

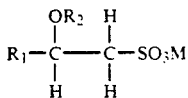

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Many additional nonsoap synthetic anionic surfactants are described in McCutcheon's, DETERGENTS AND EMULSIFIERS, ANNUAL, published by Allured Publishing Corporation, which is incorporated herein by reference. Also, U.S. Pat. No. 3,929,678, to Laughlin et al., issued Dec. 30, 1975 discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrophilic nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

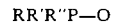

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic surfactants, useful in shampoos, can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

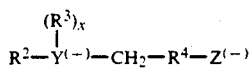

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;pO 3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane -1-phosphonate;
3-(N,N-dimethyl-N-hexadecylammonio)propane-1-sulfonate;
3-(N,N-dimethyl-N-hexadecylammonio)-2-hydroxypropane -1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1 -phosphate;
3-[P,P-dimethyl-P-dodecylphosphonio]-propane-1-phosphate; and
5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxy-ethyl) carboxy methyl betaine, stearyl bis-(2-hydroxy-propyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein the $RCONH(CH_2)_3$ radical is attached to the nitrogen atom of the betaine are also useful in this invention. The amido betaines are preferred for use in some of the compositions of this invention.

Sultaine compounds described in "Encyclopedia of Shampoo Ingredients" may also be used.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylammino-propane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. The alkyl sulfates, the ethoxylated alkyl sulfates and mixtures thereof are preferred for use herein.

Water

Water is the last essential component of the present invention's compositions and generally comprises from about 20% to about 98% of the total composition.

Optional Components

The present compositions herein can contain a variety of other optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea; thickeners and viscosity modifiers such as a diethanolamide of a long chain fatty acid (e.g., lauric diethanolamide), cocomonoethanol amide, dimethicone copolyols, guar gum, methyl cellulose starches and starch derivatives, fatty alcohols such as cetearyl alcohol, sodium chloride, sodium sulfate, polyvinyl alcohol, and ethyl alcohol; pH adjusting agents such as citric acid, lactic acid, sodium citrate, succinic acid, phosphoric acid, sodium hydroxide, sodium carbonate, etc.; coloring agents such as any of the FD&C or D&C dyes; hair oxidizing (bleaching) agents such as hydrogen peroxide, perborate and persulfate salts; hair reducing agents such as the thioglycolates; perfumes; and, sequestering agents such as disodium/tetrasodium ethylenediamine tetraacetate, polymer plasticizing agents such as glycerin and propylene glycol. Such agents generally are used individually at a level of from about 0.01% to about 10%, preferably from about 0.05% to about 5.0% by weight of the composition.

The pH of the present compositions is not critical and may be in the range of from about 3.5 to about 8.0.

As with all compositions, the present compositions should not contain components which unduly interfere with the performance of the compositions.

METHOD OF MANUFACTURE

Methods of manufacture of the present compositions are described in the following examples.

The invention will now be described with references to the following more particular examples.

EXAMPLE 1

The in situ polymerization process of the invention was carried out in a 1-liter laboratory reactor equipped with an overhead stirring motor, a metal anchor agitator, a nitrogen gas inlet tube, a water condenser connected to a bubbler, a temperature probe connected to a temperature controller and associated with a heating mantle, and a dropping funnel.

The reactor first was purged with nitrogen and charged with 400 g. of distilled water and 10 g. of Dimethicone oil having a viscosity of 100 cs. The oil-water mixture then was agitated vigorously at 350 rpm under nitrogen for 30 minutes whereupon the oil was dispersed as transparent, discrete microdroplets in the aqueous medium. The dispersion then was heated to 80° C. and 0.25 g. of di-tert-butylperoctoate was added. At this point, the mixture was maintained for 30 minutes with continuous stirring whereafter 90 g. of vinylpyrrolidone and an additional 0.25 g. of di-tert-butylperoctoate was added at one time while maintaining a nitrogen flow of 15 ml/min. After about 10-15 minutes, an exotherm was observed and the temperature increased to 86° C. The transparent, spherical droplets of oil became opaque. The the temperature was reduced to 80° C. and polymerization was continued for 6-8 hours with stirring. During this period, the dispersion became milky and the droplets became completely invisible. Polymerization was considered complete when the measured residual monomer content was less than 0.1%.

The composition obtained was a stable, homogeneous dispersion of microdroplets of Dimethicone oil stabilized in an aqueous polyvinylpyrrolidone solution. Upon exerting only slight pressure on the microdroplets, the silicone oil was observed to ooze out. However, the composition was quite stable for many months at room temperature, and for an extended period at the elevated temperature of 45° to 54° C.

EXAMPLES 2-3

The procedure of Example 1 was repeated using weight ratios of 80 g. of vinylpyrrolidone to 20 g. of Dimethicone oil (Example 2), and 70 g. of vinylpyrrolidone to 30 g. of Dimethicone oil (Example 3). Similar results to Example 1 were obtained in these runs.

EXAMPLE 4

The procedure of Example 1 was followed using a weight ratio of 20 g. of vinylpyrrolidone and 80 g. of Dimethicone oil. The resultant composition was not as viscous as in Example 1. The microdroplets obtained remained in discrete form, however, without coalescence, but settled to the bottom of the solution as a separate layer.

EXAMPLE 5

The procedure of Example 1 was followed using a weight ratio of 135 g. of vinylpyrrolidone to 15 g. of Dimethicone oil in 600 ml. of water. The results were substantially the same as obtained in Example 1.

EXAMPLE 6

The procedure of Example 1 was followed using a weight ratio of 135 g. of vinylpyrrolidone to 15 g. of a Dimethicone oil having a viscosity of 1,000 cs (mol. wt. of 28,000). The mixture was agitated at 700 rpm to produce a stable dispersion of the viscous silicone oil droplets in the aqueous polymer solution.

EXAMPLE 7

A pilot plant run was carried out in a 30 gal. reactor using two wide span turbine agitators having pitched and flat blades set at 200 rpm. 10,790 g. of vinylpyrrolidone, 1205 g. of Dimethicone oil, 100 cs, 48,225 g. of water, 120 g. of di-t-butylperoctoate, and 317 g of Germaben ® preservative were used in this run. After 6 hours, polymerization was complete and a stable, homogeneous, milky aqueous dispersion of discrete, coated silicone oil droplets was obtained which dispersion remained in discrete and suspended form throughout the composition. The composition also was stable for an extended period of time.

EXAMPLE 8

The procedure of Example 1 was followed using 90 g. of vinylpyrrolidone, 10 g of Dimethicone oil, 100 cs, 400 g. of water and 0.75 g. of Lupersol 11. The results were similar to those obtained in Example 4.

The results of these experiments are summarized in the Tables below wherein:

| VP | Vinylpyrrolidone |
|---|---|
| PVP | Polyvinylpyrrolidone |
| DM | Polydimethylsiloxane, Dimethicone, 100 cs, Petrarch Chem. Co; 1000 cs, Dow Corning Corp. |
| TBP | Tert-butyl peroctoate, e.g. Trigonox ® 21 (AKZO Chem. Co.) |
| TBPP | t-Butylperoxy pivalate, e.g. Lupersol 11 (Atochem N.A.) |
| Brookfield Viscosity | Viscosity of stabilized oil in water product in cps. as measured using a RVT spindle # 3 @ 70 rpm |

TABLE 1

| Ex. No. | Monomer | Amt (g) | Silicone Oil | Amt (g) | Viscosity (cs) | MW |
|---|---|---|---|---|---|---|
| 1 | VP | 90 | DM | 10 | 100 | 5970 |
| 2 | VP | 80 | DM | 20 | 100 | 5970 |
| 3 | VP | 70 | DM | 30 | 100 | 5970 |
| 4 | VP | 20 | DM | 80 | 100 | 5970 |
| 5 | VP | 135 | DM | 15 | 100 | 5970 |
| 6 | VP | 135 | DM | 15 | 1000 | 28,000 |
| 7* | VP | 10,790 | DM | 1205 | 100 | 5970 |
| 8 | VP | 90 | DM | 10 | 100 | 5970 |

TABLE I-A

| Ex. No. | Comonomer | Amt (g) | Medium | Amt (g) | Initiator | Amt (g) | Agitation (rpm) |
|---|---|---|---|---|---|---|---|
| 1 | — | — | Water | 400 | TBP | 0.75 | 350 |
| 2 | — | — | Water | 400 | TBP | 0.75 | 350 |
| 3 | — | — | Water | 400 | TBP | 0.75 | 350 |
| 4 | — | — | Water | 400 | TBP | 0.75 | 350 |
| 5 | — | — | Water | 600 | TBP | 0.76 | 350 |
| 6 | — | — | Water | 600 | TBP | 0.76 | 700 |
| 7* | — | — | Water | 48,225 | TBP | 120 | 200 |

TABLE I-A-continued

| Ex. No. | Comonomer | Amt (g) | Medium | Amt (g) | Initiator | Amt (g) | Agitation (rpm) |
|---|---|---|---|---|---|---|---|
| 8 | — | — | Water | 400 | TBPP | 0.75 | 350 |

*Pilot plant run

TABLE II

| Ex. No. | % Solids | Brookfield Viscosity (cps) | Diameter of Microspheres (microns) Mean | Range |
|---|---|---|---|---|
| 1 | 19.7 | 7,200 | — | — |
| 2 | 22.0 | 24,400 | | 1-14 |
| 3 | 21.1 | 17,300 | | 1-17 |
| 4 | 20.0 | — | | — |
| 5 | | | | |
| 6 | 20.6 | 10,200 | 56 | |
| 7 | 20.2 | 8,900 | 80 | 3-54 |
| 8 | 20.2 | 7,200 | — | — |

INDUSTRIAL APPLICABILITY

The present compositions are used in a conventional manner.

The following Examples further illustrate the preferred embodiments within the scope of the present invention. The Examples are given solely for the purposes of illustration and are not to be construed as limitations of the present invention as many variations of the invention are possible without departing from its spirit and scope.

The following examples are representative of the conditioning hair care compositions of the present invention.

TABLE A

CONDITIONING SHAMPOO COMPOSITION

| Components | Concentration (%) by Weight | | |
|---|---|---|---|
| Essential Components | Suitable | Preferred | Optimum |
| (a) Stabilized Silicone Product (of Exs 1-9, 20% active) | 0.25-25 | 1-10 | 2.5 |
| (b) Surfactant | 4-25 | 7-20 | 15 |
| (c) Water | qs | qs | qs |

TABLE B

PROPERTIES OF CONDITIONING SHAMPOO COMPOSITION OF INVENTION

| | Composition | | |
|---|---|---|---|
| | Suitable | Preferred | Optimum |
| pH | 4-7.5 | 5-7 | 6 |
| Viscosity, cps | 2,000-15,000 | 3,000-8,000 | 5,000 |

The following are specific examples representative of the conditioning shampoo composition of the present invention.

TABLE C

| Component | | Weight % | | |
|---|---|---|---|---|
| | | I | II | III |
| | VP/Silicone | | | |
| PVP-Silicone Product (20% active) | (90/10) Ex 1 | 15.0 | 0.0 | 0.0 |
| | (80/20) Ex 2 | 0.0 | 15.0 | 0.0 |
| | (70/30) Ex 3 | 0.0 | 0.0 | 15.0 |
| Ammonium lauryl sulfate (30% active) | | 30.9 | 30.0 | 30.5 |
| Lauric Diethanolamide (100% active) | | 5.0 | 5.0 | 5.0 |
| Preservative | | 0.5 | 0.5 | 0.5 |

TABLE C-continued

| Component | Weight % | | |
|---|---|---|---|
| | I | II | III |
| Fragrance | 0.2 | 0.2 | 0.2 |
| Water | qs | qs | qs |

The conditioning shampoo compositions of the invention exhibit excellent properties in actual use on hair including effective curl retention, enhanced hair stiffness, and advantageous curl snap, in direct comparative testing with other related products having silicone dispersed therein.

| AEROSOL CONDITIONING AND STYLING MOUSSE | | | |
|---|---|---|---|
| Essential | Suitable | Preferred | Optimum |
| PVP-Silicone (90/10, Ex. 1) (20% Active) | 0.5-10 | 1-5 | 3.0 |
| Resin (Gaffix® VC-713, GAF) | 1-10 | 2-8 | 5.0 |
| Surfactant (non-ionic, nonoxynol-9 or sodium cocoylisethionate) | 0.1-5 | 0.2-1 | 0.5 |
| Water | qs | qs | qs |
| Propellant (A-46, isobutane/propane) | 5-25 | 10-20 | 15.0 |

The following is a specific example of the conditioning mousse of the invention.

| Ingredient | % by weight |
|---|---|
| PVP-Silicone (90/10, Ex. 1) | 3.0 |
| Vinylpyrrolidone/dimethylaminoethyl methacrylate quaternized w/diethylsulfate | 5.00 |
| Oleth-20 | 0.5 |
| Fragrance | 0.25 |
| Propellant A-46 | 15.0 |
| DM DM Hydantoin | 0.25 |
| Deionized water | 76.0 |
| | 100.00 |

The expansion properties of the foam in the mousse composition is enhanced by the presence of the PVP-silicone therein. In addition, the texture and feel of the foam is smoother with the PVP-silicone present. Furthermore the mousse is effective for mending split ends of hair.

| CONDITIONER COMPOSITION | | | |
|---|---|---|---|
| | Suitable | Preferred | Optimum |
| PVP-Silicone (90/10, Ex. 1) (20% solids) | 0.5-10 | 1-5 | 2.5 |
| Emulsifier/thickener | 1-10 | 2-7 | 3.5 |
| Cationic surfactant | 0-10 | 2-5 | 3.0 |
| Water | qs | qs | qs |

The conditioner composition is effective to mend split ends of hair.

| Ingredient | % by weight |
|---|---|
| Emulsifying wax | 3.5 |
| Stearyl alcohol + Ceteareth-20 | 1.5 |
| Glycol stearate | 0.5 |
| PVP/Silicone (90/10, Ex. 1) | 2.5 |
| Laneth-16 + Ceteth-16 + Oleth-16 + Steareth-16 | 0.3 |
| Methylparaben | 0.2 |
| Propylparaben | 0.1 |

| Ingredient | % by weight |
|---|---|
| Water | qs |

In combination with the above composition, the addition of stearyl dimethylbenzyl ammonium chloride in the amount of 2-10% by weight of the composition as a cationic surfactant improves the detangling properties of the composition.

While the invention has been described with particular reference to certain embodiments thereof, it will be understood that changes and modifications may be made which are within the skill of the art. Accordingly, it is intended to be bound only by the following claims.

What is claimed is:

1. A conditioning hair care composition comprising
   (a) a stabilized silicone product obtained by in situ polymerization of a water-soluble vinyl monomer in the presence of discrete microdroplets of a silicone in water,
   (b) a surfactant, and the balance being
   (c) water.

2. A conditioning hair care composition according to claim 1 wherein said water-soluble vinyl monomer is vinyl pyrrolidone.

3. A conditioning hair care composition according to claim 2 wherein the weight ratio of the vinylpyrrolidone monomer to silicone in the polymerization mixture is about 95:5 to 5:95, respectively, on a weight basis.

4. A conditioning hair care composition according to claim 3 wherein said weight ratio is about 90:10 to about 50:50.

5. A conditioning hair care composition according to claim 3 wherein (a) is obtained as about a 20% active dispersion.

6. A conditioning hair care composition according to claim 5 comprising about 0.25 to 25% by weight of (a), about 4 to 25% by weight of (b), the balance being water.

7. A conditioner shampoo composition according to claim 6 comprising about 0.25 to 25% by weight of (a), about 4 to 25% by weight of (b), and the balance being (c) water.

8. A conditioner shampoo composition according to claim 6 comprising about 1 to 10% by weight of (a), about 7 to 20% by weight of (b), the balance being (c) water.

9. A conditioning hair care composition according to claim 2 wherein the Brookfield viscosity of the stabilized oil in water product obtained upon in situ polymerization is about 3,000 to 100,000 cps.

10. A conditioning hair care composition according to claim 1 wherein said stabilized microdroplets are homogeneously distributed throughout the resulting polymer solution.

11. A conditioning hair care composition according to claim 10 wherein said silicone is a non-volatile polyalkyl siloxane, a polyaryl siloxane, a polyalkylaryl siloxane or a polyether siloxane.

12. A conditioning hair care composition according to claim 11 wherein said silicone oil is a polydimethyl siloxane.

13. A conditioning hair care composition according to claim 1 wherein said silicone has a viscosity between about 5 to 600,000 cs.

14. A conditioning hair care composition according to claim 13 wherein said silicone has a viscosity between about 100 and 100,000 cs.

15. A conditioning hair care composition according to claim 1 wherein said in situ polymerization is carried out at a temperature of about 55° to about 85° C.

16. A conditioning hair care composition according to claim 1 wherein the particle sizes of the stabilized, discrete microdroplets of silicone are in the range of about 0.1 to 450 microns in diameter.

17. A conditioning hair care composition according to claim 16 wherein said diameter of said particles is about 1 to 100 microns, and said Brookfield viscosity of the stabilized silicone in water product is about 4,000 to 60,000 cps.

18. A conditioning hair care composition according to claim 17 wherein said Brookfield viscosity is about 6,000 to 25,000 cps.

19. A conditioning hair care composition according to claim 1 wherein the free radical polymerization initiator is oil soluble.

20. A conditioning hair care composition according to claim 1 wherein in situ polymerization is carried out under vigorous agitation of the polymerization mixture until a milky suspension is obtained and the residual monomer content of the product is less than about 0.5%.

21. A composition according to claim 1 which is a conditioner composition.

22. A composition according to claim 1 which is an aerosol conditioning means.

23. A shampoo composition comprising (a) about 0.25 to 25% by weight of a stabilized silicone product obtained by in situ polymerization of vinyl pyrrolidone in the presence of discrete microdroplets of a silicone oil in water in the weight ratio of 90:10 to 50:50, respectively, as about a 20% active composition, wherein said silicone is selected from non-volatile polyalkyl siloxane, polyaryl siloxane, polyalkyl lauryl siloxane and polyether siloxane, having a viscosity of about 5 to 600,000 cs, said discrete microdroplets of silicone being in the range of about 0.1 to 450 microns in diameter, and the Brookfield viscosity of said product is about 3,000 to 100,000 cps, (b) about 4 to 25% by weight of a surfactant, and the balance being (c) water.

24. A conditioner shampoo composition according to claim 23 wherein said silicone has a viscosity of about 100 to 100,000 cs, said discrete microdroplets have a diameter of about 1 to 100 microns, said product has a Brookfield viscosity of about 4,000 to 60,000 cps.

25. A conditioner shampoo composition according to claim 24 wherein said Brookfield viscosity is about 6,000 to 25,000 cps.

26. A conditioner shampoo composition according to claim 23 wherein said silicone is polymethyl siloxane.

27. A conditioner shampoo composition according to claim 23 wherein said weight ratio is about 90:10 to 70:30.

28. A conditioner shampoo composition according to claim 23 wherein polymerization is carried out with an oil soluble free radical initiator.

* * * * *